United States Patent [19]

Lersmacher et al.

[11] Patent Number: 4,537,506
[45] Date of Patent: Aug. 27, 1985

[54] ATOMIZER FOR ATOMIC ABSORPTION SPECTROSCOPY

[76] Inventors: Bernhard Lersmacher, Schlossweiherstrasse 31, 5100 Aachen, Fed. Rep. of Germany; Michael P. Wassall, 32 Greenfields, Earith, Cambridge; Philip J. Connor, 5 Mereton Walk, Hardwick, Cambridge, both of England

[21] Appl. No.: 433,760

[22] Filed: Oct. 12, 1982

[30] Foreign Application Priority Data

Oct. 12, 1981 [DE] Fed. Rep. of Germany ....... 3140458

[51] Int. Cl.³ ........................ G01N 21/16; G01J 3/30
[52] U.S. Cl. .................... 356/312; 219/275; 219/271
[58] Field of Search ............. 219/271, 276, 272, 273, 219/275; 427/49, 50, 51; 118/726, 727, 50.1, 620; 432/264, 265; 356/244, 312

[56] References Cited

U.S. PATENT DOCUMENTS

| | | | |
|---|---|---|---|
| 4,111,563 | 9/1978 | Tamm | 219/271 |
| 4,204,769 | 5/1980 | Lersmacher | 219/271 |

FOREIGN PATENT DOCUMENTS

| | | | |
|---|---|---|---|
| 2225421 | 12/1973 | Fed. Rep. of Germany | 356/312 |
| 2334416 | 1/1974 | Fed. Rep. of Germany | 356/244 |
| 2825759 | 12/1979 | Fed. Rep. of Germany | 356/312 |

OTHER PUBLICATIONS

Chakrabarti, C. L., "Capacitive Discharge Heating in Graphite Furnace . . . ", Anal. Chem., Jan. 1980, 52, No. 1, pp. 167-176.
Batley, Graeme E., "Determination of Heavy Metals . . . ", Analy. Chem., vol. 49, No. 13, Nov. 1977, pp. 2031-2035.
Massmann, H., "Vergleich von Atomabsorption . . . ", Spectrochimica Acta, 1968, vol. 23B, pp. 215-226.

*Primary Examiner*—C. C. Shaw
*Assistant Examiner*—Teresa J. Walberg
*Attorney, Agent, or Firm*—Paul R. Miller

[57] ABSTRACT

The atomizer of the present invention serves for generating free atoms and an atomic cloud by heating a sample for analysis. The device includes a preferably tubular cuvette for receiving the sample, and the cuvette consists either of a basic body of carbon, which is enveloped by a pyrolytic graphite layer, or only of pyrolytic graphite layers. An electric supply unit for Joule heating the cuvette is in contact with the cuvette by contact members. In order to achieve a radial temperature distribution in the cuvette such that the inner wall of the cuvette is at an essentially higher temperature than the outer wall of the cuvette, the contact surfaces of the cuvette and the contact surfaces of the contact members contact each other in such a manner that the electric current applied during operation of the atomizer preferably flows through the inner wall of the cuvette.

10 Claims, 13 Drawing Figures

ATOMIZER FOR ATOMIC ABSORPTION SPECTROSCOPY

The invention relates to an atomizer for producing free atoms and an atomic cloud for atomic absorption spectroscopy by heating an analysis sample, with the atomizer having a preferably tubular cuvette for receiving the sample, in which the cuvette consists either of a basic member of carbon which is enveloped by a layer of pyrolytic graphite, or consists only of pyrolytic graphite, and having an electric supply unit for Joule heating the cuvette for producing the free atoms of the sample, the supply unit and the cuvette being in contact with each other via contact members, and the cuvette and the contact members being constructed so that a desired temperature distribution in the cuvette is obtained.

A comparable device is known from DE-OS No. 23 34 416. In this specification the atomizer is referred to as a "furnace" and the cuvette as a "furnace element". The cuvette of this device consists of graphite, or of pyrolytic graphite, or of graphite which is coated with a layer of pyrolytic graphite, and is constructed so that, when an electric current flows between contact members (termed "electrode bodies") connected at the two ends of the cuvette, a temperature distribution along the longitudinal axis of the cuvette is obtained such that the area comprising the sample reaches a higher temperature than areas in the proximity of the ends of the cuvette. This temperature distribution has the disadvantage that high thermal radiation and hence high current consumption occurs. It is known from DE-AS No. 22 19 594 to avoid losses of thermal radiation by surrounding the surfaces of a cuvette remote from the sample and atomic cloud with a radiation-absorbing protective sheath having poor thermal dissipation, which cuvette is neither coated with a layer of pyrolytic graphite nor consists of pyrolytic graphite. The protecting sheath consists either of porous carbon or is a solid tube which surrounds the cuvette at a distance and is fixed in a holder at one end. According to DE-OS No. 22 25 421 the heating of a cuvette which is neither coated with a layer of pyrolytic graphite nor consists of pyrolytic graphite occurs by means of a heating member through which a current flows and which surrounds the cuvette and consists of a porous or foamed electrically conductive material, for example, porous graphite or porous carbon. In this case also, thermal losses must be kept as small as possible. Such protective sheaths and heating members which may be considered as envelopes have the disadvantage that the total construction becomes more complex and consequently also more expensive. Protective envelopes or heating elements, in particular those of porous material, suffer from increased corrosion, for example by oxidation or by reaction with the analysis sample, and must be replaced more or less frequently. The measuring operation itself and, in particular, loading the analysis sample, becomes more difficult and requires additional equipment.

It is an object of the invention to obtain a temperature distribution such that, not only the area comprising the analysis sample also reaches the highest temperature, measured along the axis of the cuvette, but that in addition a radial temperature distribution is achieved in the generally rotationally symmetrical cuvette such that the inner wall of the cuvette has a substantially higher temperature than the outer wall of the cuvette.

In accordance with the invention the contact surfaces of the cuvette on the one hand and the contact surfaces of the contact members on the other hand are so constructed and contact each other in such manner that the electric current applied during operation of the atomizer preferably flows through the inner wall and through the inner pyrolytic graphite layer of the cuvette.

The invention provides the possibility of realizing in the wall of the cuvette a steep temperature gradient having temperatures which decrease from the inside to the outside. The advantage of this measure consists in a substantially better energy balance as regards the required electrical energy and moreover is also of great influence on the speed of the performance of the analysis and hence on the quality of the performed analytical determination.

The fundamental idea of the invention consists in that certain parts of the cuvette, under optimum use of the physical properties of the materials of the cuvette, preferably take over the current conduction, whereas other parts of the cuvette simultaneously serve as heat flow barriers from the inside to the outside. In this connection, pyrolytic graphite, a well oriented, stratified, strongly anisotropic form of graphite, is of particular importance as a material component since it has very good electrical and thermal conductivity values parallel to the strata, whereas the same conductivities, measured normal to the strata, are smaller by orders of magnitude, in the thermal case a hundred fold, and in the electrical case a thousand-fold. This pronounced anisotropy of pyrolytic graphite enables selective energy dissipation and selective heating, respectively.

The contact members preferably are connected to the pyrolytic graphite layers on the inner wall of the cuvette.

In the case of a cuvette which consists of a basic member, for example of graphite, with an enveloping layer of pyrolytic graphite, the insulating effect of the outer pyrolytic graphite layer is preferably further increased by interrupting the pyrolytic graphite layer enveloping the basic member of the cuvette in places which are preferably located between the contact surfaces and the outer pyrolytic graphite layer. These interruptions impede the flow of current and heat from the inside to the outside, but not along the readily conductive layers. The interruptions are provided by means of mechanical processing methods, for example by grinding, turning or milling, between the subsequent contact surfaces and the outer pyrolytic graphite layer. The interruptions, for example, have the shape of gaps, grooves or slots extending around the circumference.

The basic body of the cuvette consists, for example, of electrographite, pyrolytic graphite, vitreous carbon, foamed carbon, carbonized laminated fabric or carbonized hard-paper. Cuvettes having a basic body of carbonized laminated fabric are known from DE-OS No. 27 02 189. Carbonized hardpaper is manufactured by carbonization of a laminated material based on phenol resin/paper.

The pyrolytic graphite layer is provided on the basic body by reactive deposition from a hydrocarbon-containing gaseous phase. The direction of growth of the pyrolytic graphite layer is normal to the wall of the basic body.

The contact surfaces of the cuvette are preferably constructed so that the electric current applied during operation of the device extends at right angles to the direction of growth through the inner pyrographic layer.

According to another preferred embodiment of the invention the contact surfaces of the cuvette are constructed so that the electric current applied during operation of the device flows through the basic body.

The electric contacting according to the invention which is provided, for example, by grinding and facetting, respectively, of cuvette and contact members as well as providing gaps, grooves or slots operative as current and thermal flow barriers has the advantage that the main current flow occurs through the inner wall area of the cuvette, as a result of which the interior of the cuvette is heated preferentially. Moreover the heat flow in the radial direction, and so through the wall to the exterior, is considerably impeded.

A few embodiments of the invention are shown in the drawings, in which:

FIG. 1 shows diagrammatically an atomizer for the atomic absorption spectroscopy, FIGS. 2a to 2c are longitudinal sectional views of a few typical cuvettes, FIGS. 3a and 3b show a few examples of the design of the contact surfaces of the cuvettes, FIG. 4 shows the general contact arrangement between cuvette and contact members, and FIGS. 4a to 4f show a few contact arrangements for use in apparatus according to FIG. 4.

In the FIG. 1 device, a cuvette 1, which has an aperture 2 for injection of a sample solution (a few microliters) to be analysed, is arranged between two contact members 3. The contact members 3 are incorporated in an electrical supply unit 4. Above the cuvette 1 an aperture 5 is present through which a sample can be introduced into the cuvette and which can be closed by means of a stopper 6.

FIGS. 2a to 2c are each longitudinal sectional views of two tubular cuvettes 1 each having a basic body 7 and an aperture 2. FIG. 2a shows cuvettes of graphite without a pyrolytic graphite layer.

FIG. 2b shows cuvettes each having a completely enveloping pyrolytic graphite layer 8.

In FIG. 2c, the pyrolytic graphite layer 8 is interrupted at the places indicated by the arrows 9, that is to say they have current and heat flow barriers, or in other words, the inner pyrolytic graphite layer 8a is separated from the remaining pyrolytic graphite layer 8.

FIG. 3a shows an example of the design of the contact surfaces 10 of a cuvette consisting only of pyrolytic graphite. In this cuvette, the basic body 7 and the strata consist of one and the same material. FIG. 3b shows a cuvette consisting of graphite 7 with a layer of pyrolytic graphite.

In FIGS. 3a and 3b the cuvettes show contact surfaces 10 for feeding the electric current.

The contact surfaces 10 are manufactured by mechanical treatment, for example by grinding, the ground surface being preferably chosen so that the electric current applied during operation of the device flows through the inner-most pyrolytic graphite layers at right angles to the direction of growth.

FIG. 3b shows in addition an interruption 11 of the pyrolytic graphite layer 8 through which the basic body 7 is exposed and the layer 8 is separated from the inner pyrolytic graphite layer 8a.

At this place 11, produced by grinding, the flow of current and heat are impeded.

FIG. 4 shows a cuvette 1 of pyrolytic graphite with aperture 2 and having two contact members 3. The direction of the good thermal and electric conductivity of the pyrolytic graphite is denoted by an arrow $<a>$, that of the poor conductivity by an arrow $<c>$.

FIGS. 4a to 4f show diagrammatically various forms of ground contact ends (that is to say the contact surfaces) of tubular cuvettes which consist either only of pyrolytic graphite (FIGS. 4a to 4d) or of basic bodies 7 having pyrolytic graphite layers 8 and 8a (FIG. 4e and 4f)

FIG. 4a shows a contact end of the cuvette 1 connected by an internal contact to the contact member 3, contact being made either by a press fit over the whole inner circumference or by spreading contacts which touch the inner circumference of the cuvette only at a few points or places.

FIG. 4b shows a contact end of the cuvette 1 ground at an angle (for example of 30°, measured to the longitudinal axis) and the contact member 3 engages the cuvette 1 under a pressure.

As compared with the embodiment of FIG. 4a, this embodiment has the advantage that the measuring beam is not limited in width by the contact member.

Figure 1:
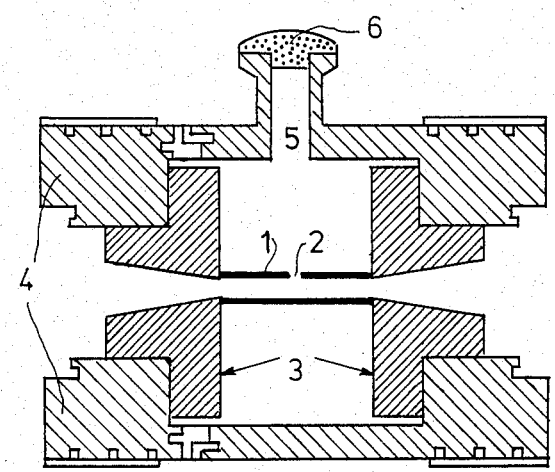
Figure 2A:
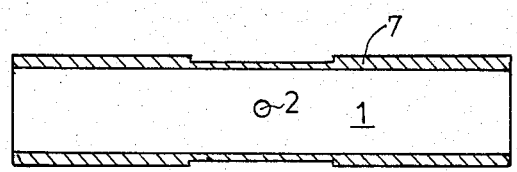
Figure 2A:
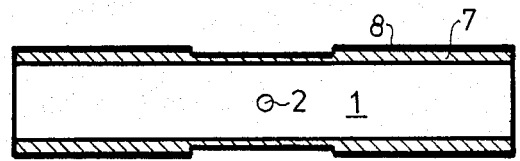
Figure 2B:
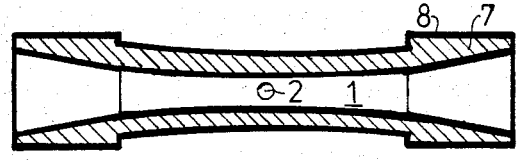
Figure 2B:
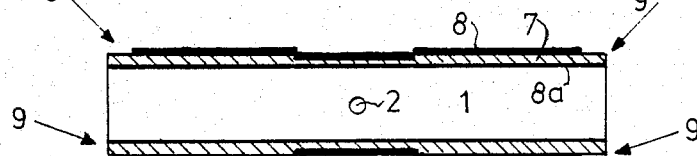
Figure 2C:
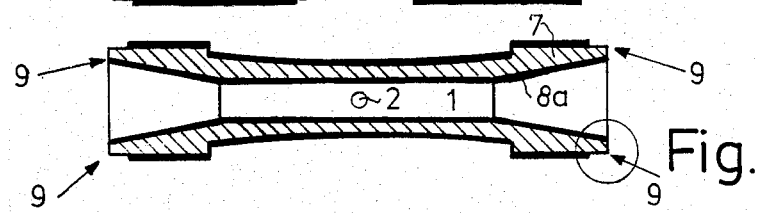
Figure 3A:
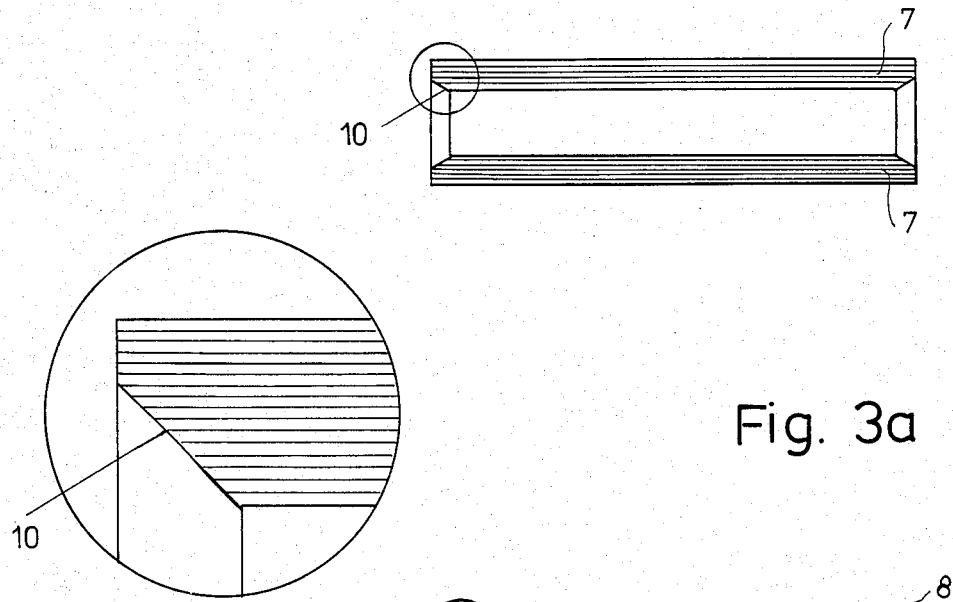
Figure 3B:
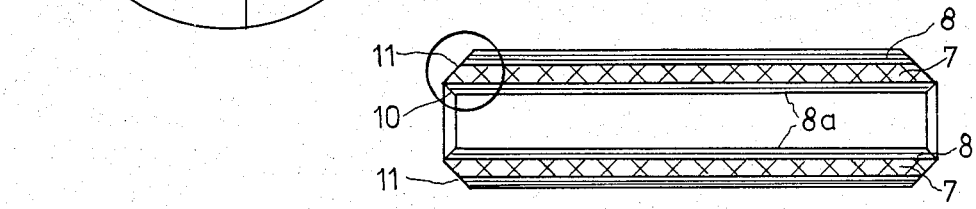
Figure 3B:
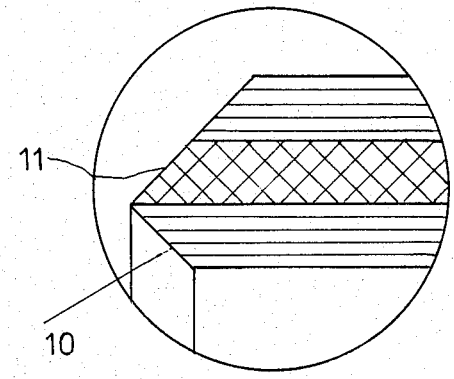
Figure 4:
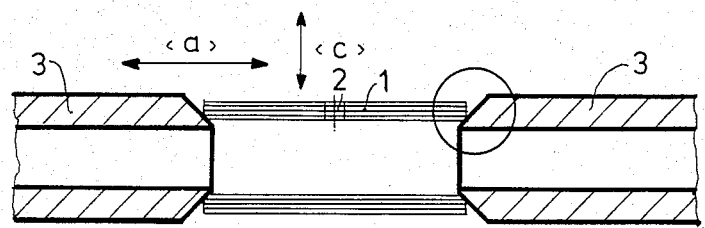
FIG. 4c shows a type of end grinding (grinding angle approximately 5° to 30°) by which a smaller thermal contact and a more homogeneous temperature distribution along the longitudinal axis of the cuvette is produced.
FIG. 4d shows a stepped end grinding which, like that of FIG. 4b, does not involve a limitation of the measuring beam.
Figure 4A:
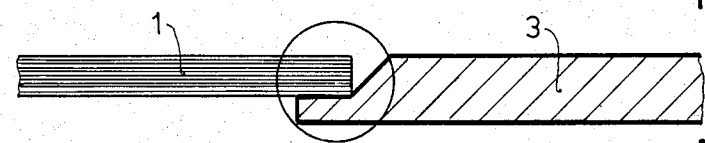
Figure 4B:
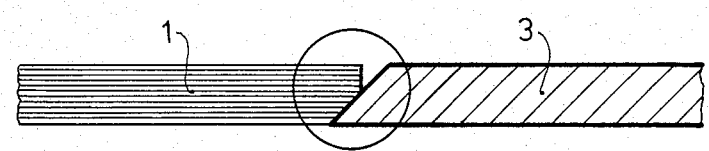
Figure 4C:
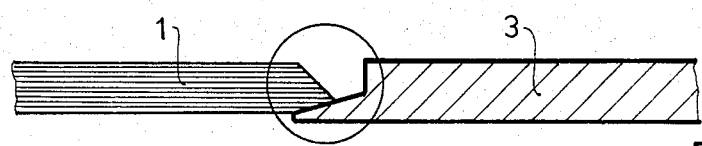
Figure 4D:
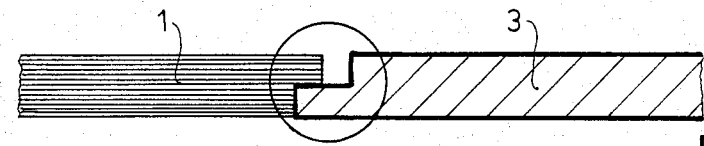
Figure 4E:
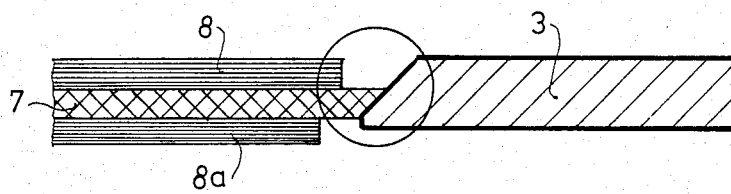
Figure 4F:
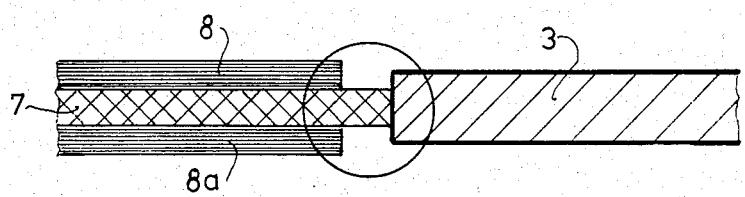

FIGS. 4e and 4f show embodiments having contact only to the basic body 7 which consists of electrographite or vitreous carbon. The outer layer 8 of pyrolytic graphite only serves for heating insulation. The inner layer 8a may be omitted, if desired.

The contact members 3 are, for example, in the form of hollow bodies or of porous bodies. Suitable materials for the manufacture of the contact members are, for example, electrographite, vitreous carbon, porous vitreous carbon and metals, for example copper. If desired, the contact members are provided with or connected to cooling devices.

Temperature measurements were performed on cuvettes which consisted only of pyrolytic graphite having a wall thickness of approximately 800 micrometers, with contacts according to FIGS. 4a or 4b, which measurements proved that the temperature difference between the inner wall and the outer wall is already evident at low temperatures of approximately 600° C., is approximately 40° at 1,000° and more than 100° at 1,200° C. on the outer wall.

These values were measured in the stationary condition, i.e. after reaching temperature equilibrium, so they are considerably larger in the dynamic state used in atomic absorption spectroscopy. Measurements have confirmed that at high operating temperatures up to 3,000° C. in the real analysis cycle, temperature differences of more than 1,000° occur between the inside and the outside of the cuvette.

What is claimed is:

1. An atomizer for producing free atoms and an atomic cloud for atomic absorption spectroscopy comprising
   a tubular cuvette for receiving a sample, said cuvette being at least outwardly enveloped by layers of pyrolytic graphite, electrical supply means for Joule heating said cuvette to produce free atoms of said sample, contact member means for contacting said cuvette and said electrical supply means, wherein said cuvette and said contact member means are constructed to obtain a predetermined temperature distribution in said cuvette, first contact surfaces of said cuvette and second contact surfaces of said contact member means being constructed so that electric current flows from said electrical supply means through an inner wall of said cuvette by way of said contact member means, and interruptions of said pyrolytic graphite layers between said first contact surfaces and outer surfaces of said cuvette.

2. An atomizer according to claim 1, wherein said cuvette consists entirely of pyrolytic graphite layers.

3. An atomizer according to claim 2, wherein said contact member means is connected to said pyrolytic graphite layers at an inner wall of said cuvette.

4. An atomizer according to claim 2, wherein said first contact surfaces are constructed so that said electric current flows through inner pyrolytic graphite layers at right angles to thicknesses of said pyrolytic graphite layers.

5. An atomizer according to claim 1, wherein said tubular cuvette consists of a basic body structure enveloped by said layers of pyrolytic graphite.

6. An atomizer according to claim 5, wherein said first contact surfaces are constructed so that said electric current flows through said basic body structure.

7. An atomizer according to claim 5, wherein first contact members are provided by said basic body structure.

8. An atomizer according to claim 5, wherein said basic body structure consists of carbonzied hardpaper.

9. An atomizer according to claim 1, wherein said interruptions impede flow of said electric current and heat between said cuvette and said contact member means.

10. An atomizer according to claim 1, wherein said interruptions are one of gaps, grooves, and slots extending circumferentially around said cuvette.

* * * * *